US008377050B2

(12) United States Patent
Lentz et al.

(10) Patent No.: US 8,377,050 B2
(45) Date of Patent: Feb. 19, 2013

(54) CRYO-APPLICATOR CROSS-SECTION CONFIGURATION

(75) Inventors: David J. Lentz, La Jolla, CA (US); Jillian K. Allen, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1405 days.

(21) Appl. No.: 11/760,564

(22) Filed: Jun. 8, 2007

(65) Prior Publication Data
US 2008/0306475 A1 Dec. 11, 2008

(51) Int. Cl.
*A61B 18/02* (2006.01)
(52) U.S. Cl. ......................................................... 606/23
(58) Field of Classification Search .............. 606/20–26
See application file for complete search history.

(56) References Cited

U.S. PATENT DOCUMENTS

| | | | | |
|---|---|---|---|---|
| 4,946,460 A * | 8/1990 | Merry et al. | ..................... | 606/24 |
| 4,960,411 A | 10/1990 | Buchbinder | | |
| 5,042,985 A | 8/1991 | Elliott et al. | | |
| 5,224,943 A | 7/1993 | Goddard | | |
| 5,281,213 A * | 1/1994 | Milder et al. | ..................... | 606/15 |
| 5,656,030 A | 8/1997 | Hunjan et al. | | |
| 5,715,817 A | 2/1998 | Stevens-Wright et al. | | |
| 5,992,158 A * | 11/1999 | Goddard et al. | ................ | 62/51.2 |
| 6,074,412 A | 6/2000 | Mikus et al. | | |
| 6,235,019 B1 | 5/2001 | Lehmann et al. | | |
| 6,270,493 B1 | 8/2001 | Lalonde et al. | | |
| 6,468,268 B1 | 10/2002 | Abboud et al. | | |
| 6,485,455 B1 * | 11/2002 | Thompson et al. | ........ | 604/95.04 |
| 6,575,966 B2 | 6/2003 | Lane et al. | | |
| 6,585,728 B2 | 7/2003 | Heiner et al. | | |
| 6,586,717 B2 * | 7/2003 | Vrehen et al. | ............. | 250/201.5 |
| 6,589,234 B2 * | 7/2003 | Lalonde et al. | .................. | 606/23 |
| 6,629,972 B2 | 10/2003 | Lehmann et al. | | |
| 6,669,689 B2 | 12/2003 | Lehmann et al. | | |
| 6,981,382 B2 * | 1/2006 | Lentz et al. | ...................... | 62/119 |
| 2002/0062122 A1 | 5/2002 | Lehmann et al. | | |
| 2003/0009160 A1 | 1/2003 | Carroll et al. | | |
| 2003/0018326 A1 | 1/2003 | Abboud et al. | | |
| 2004/0034365 A1 * | 2/2004 | Lentz et al. | .................... | 606/108 |
| 2004/0054363 A1 | 3/2004 | Vaska et al. | | |
| 2005/0288657 A1 * | 12/2005 | Lentz et al. | ...................... | 606/21 |
| 2006/0004350 A1 * | 1/2006 | Ryba | ............................... | 606/21 |

* cited by examiner

*Primary Examiner* — Michael Peffley
*Assistant Examiner* — Ronald Hupczey, Jr.
(74) *Attorney, Agent, or Firm* — Seager, Tufte & Wickhem, LLC

(57) ABSTRACT

A configuration for a cryo-catheter which optimizes both the catheter's outer diameter and the size of the catheter's internal refrigerant flow path is described. Specifically, the inner dimensions of the cryo-catheter are configured to accommodate a pre-selected flow of refrigerant into the catheter's distal tip, and a return flow of refrigerant from the distal tip. The return flow is established in the void spaces between a refrigerant supply line and the inner wall of the catheter body. The available void space varies along the catheter length and depends on the presence/absence of various catheter accessories (i.e. pull wires, pressure tubes, etc.) which typically only extend through a portion of the catheter length. The disclosed configuration ensures that the cryo-catheter does not operate in a refrigerant limited condition, maintains the refrigerant as a liquid in the supply tube, and maintains the return line pressure at about 1 atmosphere.

20 Claims, 2 Drawing Sheets

CRYO-APPLICATOR CROSS-SECTION CONFIGURATION

FIELD OF THE INVENTION

The present invention pertains generally to systems and methods for cryoablating tissue. More particularly, the present invention pertains to a configuration for a cryo-catheter having an active articulation system. The present invention is particularly, but not exclusively, useful as a configuration for a cryo-catheter which optimizes both the catheter's outer diameter and the size of the catheter's internal refrigerant flow path.

BACKGROUND OF THE INVENTION

Cryoablation has been successfully used in various medical procedures to destroy or deactivate selected tissues. In this context, it has been determined that cryoablation procedures can be particularly effective for curing heart arrhythmias, such as atrial fibrillation. It is believed that at least one-third of all atrial fibrillations originate near the ostia of the pulmonary veins, and that the optimal treatment technique is to treat these focal areas through the creation of circumferential lesions around the ostia of these veins.

Typically, to cryoablate selected tissue in and around the heart in a non-invasive procedure, a cryo-catheter Is employed. In this regard, tissue in and around the heart is typically accessed from a peripheral artery such as the femoral or brachial artery. From the peripheral artery, the distal end of the catheter must navigate through the curves and bends of a narrow and tortuous vascular tree to reach a targeted area. In some cases, an introducer sheath is first inserted into the vasculature to establish a mechanical pathway to the treatment site. This allows the cryo-catheter to pass within the sheath from the peripheral artery to the treatment site. To be successful in locating the distal tip of a cryo-catheter at a treatment site, it is important that the catheter be flexible and have a relatively small outside diameter. On the other hand, modern cryo-catheters typically require the incorporation of a number of sophisticated, internal catheter systems that must all somehow fit within the thin, low profile catheter. These systems often include a first passageway to deliver a refrigerant from an extracorporeal location to the distal tip for expansion at the distal tip. A second passageway is also required to evacuate the expanded refrigerant from the tip.

In addition to the internal systems described above, various monitoring systems are often employed to measure tip temperature, tip pressure and electrical signals from the heart (i.e. EKG signals). These systems often require pressure tubes, wires, sensors, electrode bands and other monitoring components. Lastly, but perhaps equally important, modern cryo-catheters often include internal systems to articulate the distal tip of the catheter. These articulation systems can be used to steer the cryo-catheter during its journey through the vasculature and to manipulate the distal tip of the catheter into contact with selected tissue at a treatment site. For this purpose, these articulation systems typically include pull wires, sheath springs, deflection support structures such as springs, and other peripheral components. Thus, all of these system components need to somehow fit within a low profile cryo-catheter while still leaving sufficient room along the entire length of the catheter to deliver an ample quantity of refrigerant to the distal tip and evacuate expanded refrigerant from the tip.

With the above in mind, for a typical medical procedure, cryoablation begins at temperatures below approximately minus twenty degrees Centigrade ($-20°$ C.). For the effective cryoablation of tissue, however, much colder temperatures are preferable. With this goal in mind, various fluid refrigerants (e.g. nitrous oxide $N_2O$) have normal boiling point temperatures (i.e. the boiling point temperature at 1 atmosphere pressure) as low as minus eighty eight degrees Centigrade ($-88°$ C). An important consideration in this regard is the fact that the temperature at which a refrigerant boils is dependant on the pressure that the refrigerant is experiencing. Specifically, for a refrigerant such as nitrous oxide, the boiling temperature increases with increases in boiling pressure.

A low ablation temperature, however, is typically not sufficient to efficiently cryoablate tissue. Specifically, it is also necessary that there is a sufficient refrigeration potential to effectively freeze tissue. In order for a system to both attain and maintain a suitable cryoablation temperature, while providing the necessary refrigeration potential to effect cryoablation of tissue, several physical factors need to be considered.

In this regard, it is well known that when a fluid boils (i.e. changes from a liquid state to a gaseous state) a significant amount of heat is transferred to the fluid from its surroundings. With this in mind, consider a liquid that is not boiling, but which is under a condition of pressure and temperature wherein effective evaporation of the liquid ceases. A liquid in such condition is commonly referred to as being "fully saturated." It will then happen, as the pressure on the saturated liquid is reduced, the liquid tends to boil and extract heat from its surroundings. Initially, the heat that is transferred to the fluid is generally referred to as latent heat. More specifically, this latent heat is the heat that is required to change a fluid from a liquid to a gas, without any change in temperature. For some fluids, this latent heat transfer can be considerable. In this context, the refrigeration potential is a measure of the capacity of a system to extract energy from its surroundings at a fixed temperature.

An important consideration for the design of any refrigeration system is the fact that heat transfer is proportional to the difference in temperatures ($\Delta T$) between the refrigerant and the body that is being cooled. Importantly, heat transfer is also proportional to the amount of surface area of the body being cooled (A) that is in contact with the refrigerant. In addition to the above considerations (i.e. $\Delta T$ and A); when the refrigerant is a fluid, the refrigeration potential of the refrigerant fluid is also a function of its mass flow rate. Specifically, the faster a heat-exchanging fluid refrigerant can be replaced (i.e. the higher its mass flow rate), the higher the refrigeration potential will be. This notion, however, has it limits.

As is well known, the mass flow rate of a fluid through a duct/tube results from a pressure differential on the fluid. More specifically, it can be shown that as a pressure differential starts to increase on a refrigerant fluid in a system, the resultant increase in the mass flow rate of the fluid will also increase the refrigeration potential of the system. This increased flow rate, however, creates additional increases in the return pressure (i.e. back pressure) that will result in a detrimental increase in the boiling point temperature of the refrigerant. Thus, for relatively low mass flow rates, increases in the mass flow rate of the refrigerant will cause lower temperatures. Refrigerant flow in this range is said to be "refrigeration limited." On the other hand, for relatively high mass flow rates, increases in the mass flow rate actually cause the temperature of the refrigerant to rise. Flow in this range is said to be "surface area limited." Because a cryo-catheter refrigeration system is least efficient at higher temperatures, operation under "refrigeration limited" conditions is generally avoided.

From the above discussion, it can be appreciated that a cryo-catheter refrigeration system must be capable of performing three basic functions. First, it must deliver the refrigerant to the distal tip of the cryo-catheter in a liquid state so that the liquid can boil at the tip and absorb latent heat. Second, the system must evacuate the expanded refrigerant and maintain the pressure where the refrigerant boils at a preselected pressure to ensure that the refrigerant boils at a low temperature. Lastly, the system must perform the first two functions at a sufficient refrigerant mass flow rate to generate the necessary refrigeration potential to efficiently cryoablate tissue. It is to be further appreciated that the satisfaction of these three requirements is highly dependent on the size of the flow passages and expansion chambers used to deliver the refrigerant to the cryo-catheter's distal tip and evacuate the expanded refrigerant from the tip.

In light of the above, it is an object of the present invention to provide a cryo-catheter configuration which optimizes both the catheter's outer diameter and the size of the catheter's internal refrigerant flow path. It is another object of the present invention to provide a cryo-catheter configuration that ensures that the cryo-catheter does not operate in a refrigerant limited condition. It is yet another object of the present invention to provide a configuration for a cryo-catheter that cooperates to maintain a refrigerant in a liquid state as it transits through a supply tube and simultaneously maintains the pressure in a refrigerant return line at about 1 atmosphere. Yet another object of the present invention is to provide a cryo-catheter configuration which is easy to assemble, relatively simple to implement, and comparatively cost effective.

SUMMARY OF THE INVENTION

The present invention is directed to a configuration for a cryo-catheter which optimizes both the catheter's outer diameter and the size of the catheter's internal refrigerant flow path. In particular, the outer diameter of the catheter is minimized to allow the catheter to be advanced, percutaneously, through a patient's vasculature. On the other hand, the inner dimensions of the cryo-catheter are configured to accommodate a pre-selected flow of refrigerant into the catheter's distal tip, and importantly, a return flow of refrigerant from the distal tip.

In greater structural detail, the cryo-catheter has a proximal end and a distal end and includes a tip at the distal end. The proximal end of the cryo-catheter is attached to a catheter handle. Between the handle and the tip, the cryo-catheter includes a two-part catheter body having an articulation segment and a braided segment. The braided segment extends distally from the catheter handle to the proximal end of the articulation segment. For the cryo-catheter, the articulation segment is positioned between the distal end of the braided segment and the cryo-catheter tip. Together, the braided segment and articulation segment establish a central lumen which extends from the catheter handle to the catheter tip. With this cooperation of structure, the central lumen has a first cross-sectional area in the articulation segment and a second cross-sectional area in the braided segment.

To cool the cryo-catheter's distal tip, a two-part refrigerant supply line is disposed in the central lumen. More specifically, the supply line includes a high pressure supply tube and a flow restricting tube (e.g. capillary tube). Structurally, the capillary tube is attached to and extends from a distal end of the high pressure supply tube. In the operation of the cryo-catheter, a regulated flow of liquid refrigerant is introduced into the proximal end of the high pressure supply tube. With this arrangement, the refrigerant traverses the supply tube, passes through the capillary tube and then outflows into an expansion chamber at the cryo-catheter's distal tip. Expanded refrigerant is then exhausted from the chamber through a low pressure return line that is established in the void spaces between the outer wall of the supply line and the inner wall of the catheter body. It is important to note that the exact nature and dimensions of these void spaces varies along the length of the cryo-catheter. Specifically, at each location along the length of the catheter, the available void space will depend on the size and extent of other catheter structures (i.e. accessories) that are present in the central lumen at that particular location. These catheter accessories can include, but are not necessarily limited to, pull wires, sheath springs, sheath spring guide tubes, thermocouple wires, electrode wires and pressure measurement tubes. For the cryo-catheter, each of these accessories extends through some or all of the length of the catheter.

The dimensions of the refrigerant flow paths are functionally significant and typically must be sized with several operational objectives in mind. Specifically, these dimensions control the pressures and flow rates at critical points along the refrigerant flow path. In greater detail, the pressure within the high pressure supply tube must be sufficient to maintain the refrigerant in a liquid state throughout the length of the supply tube. On the other hand, the pressure in the expansion chamber must be sufficiently low to allow for full refrigerant vaporization within the chamber. As a consequence, the capillary tube must create the necessary pressure reduction between the high pressure supply tube and the low pressure expansion chamber.

In addition to the requirements described above, the refrigerant pressures and flow path dimensions are generally designed to avoid operation of the cryo-catheter in a refrigerant limited condition. This condition is typically characterized as having a relatively low supply pressure for refrigerant entering the supply tube together with a relatively low return pressure. In the refrigerant limited condition, the catheter is typically unable to achieve the lowest possible cryoablation temperature at the catheter's distal tip. Quantitatively, the expansion chamber is generally maintained at a pressure of approximately 1 atm. In addition, the accessories and fluid supply line are arranged to leave a portion of a first cross-sectional area void in the articulation segment and leave a portion of said second cross-sectional area void in the braided segment. These voids establish a return path for a flow of gaseous refrigerant through the central lumen. Preferably, the cryo-catheter is configured with the second cross-sectional area void being greater than about thirty percent of the first cross-sectional area. As a consequence, the return path in the articulation segment has a somewhat greater flow capacity than the return path in the braided segment. With this interactive cooperation of structure, refrigerant is maintained as a liquid in the high pressure supply tube while maintaining the expansion chamber at a pressure of about 1 atm. to ensure that the cryo-catheter does not operate in a refrigerant limited condition.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
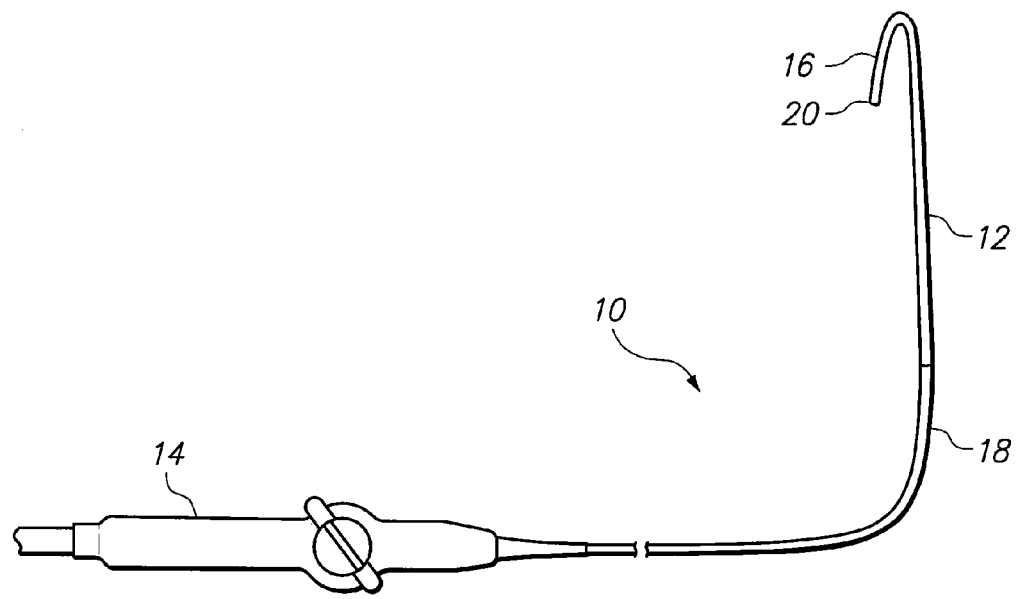
FIG. 1 is a perspective view of a cryo-catheter and catheter handle in accordance with the present invention.

Referring initially to FIG. 1, a system (generally designated 10) having a cryo-catheter 12 and catheter handle 14 is shown. For the present invention, the system 10 can be used as part of a cryoablation apparatus to cryoablate a lesion in a body conduit of a patient (patient not shown). Although the system 10 is described herein for a catheter 12, those skilled in the pertinent art will appreciate that the systems and methods described herein can be implemented with other applicators such as a cryo-probe (not shown) that is configured to contact and ablate exposed tissue.

As indicated in FIG. 1, the cryo-catheter 12 includes an articulation segment 16 that can be deflected using the catheter handle 14 into different configurations and orientations. FIG. 1 further shows that the cryo-catheter 12 includes a braided segment 18 that extends distally from the catheter handle 14 to the articulation segment 16. It can be further seen that the cryo-catheter 12 includes a distal tip 20 that is attached to and extends distally from the articulation segment 16. In use, the distal tip 20 of the cryo-catheter 12 is typically inserted into a patient through a peripheral artery, such as the femoral artery, and advanced through the patient's vasculature until the distal tip 20 is positioned at a targeted location such as a location inside a heart chamber. Although the system 10 is capable of performing a cryoablation procedure in an upper body vessel, such as a pulmonary vein, those skilled in the pertinent art will quickly recognize that the use of the system 10, as herein described, is not limited to use in any one type of vessel, but, instead can be used in vascular conduits and other ductal systems throughout the human body.

Figure 2:
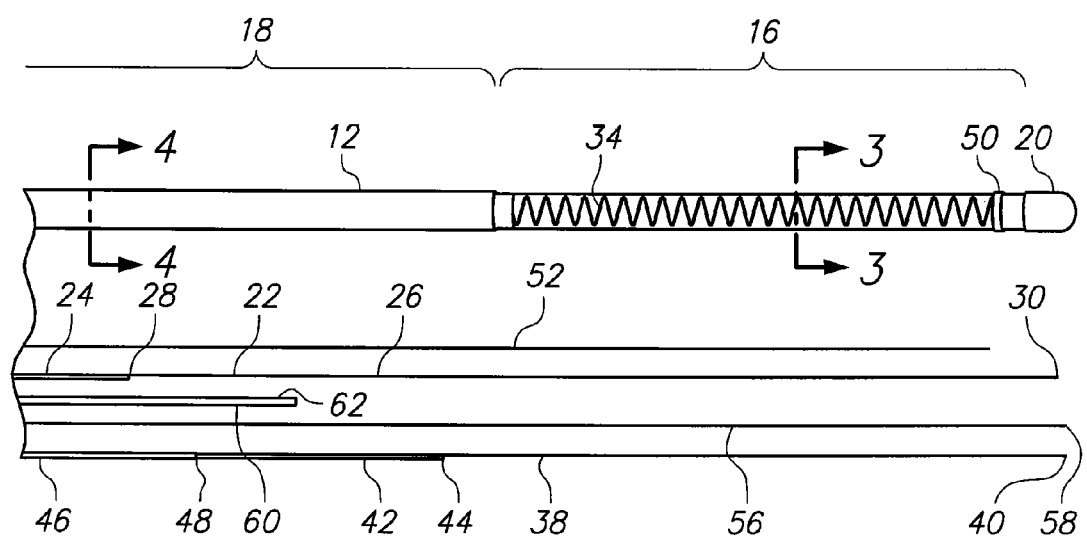
FIG. 2 is a side plan view of a distal portion of the cryo-catheter shown in FIG. 1, shown juxtaposed with a layout of internal catheter accessories to illustrate the distal extent of each of the catheter accessories.
Figure 3:
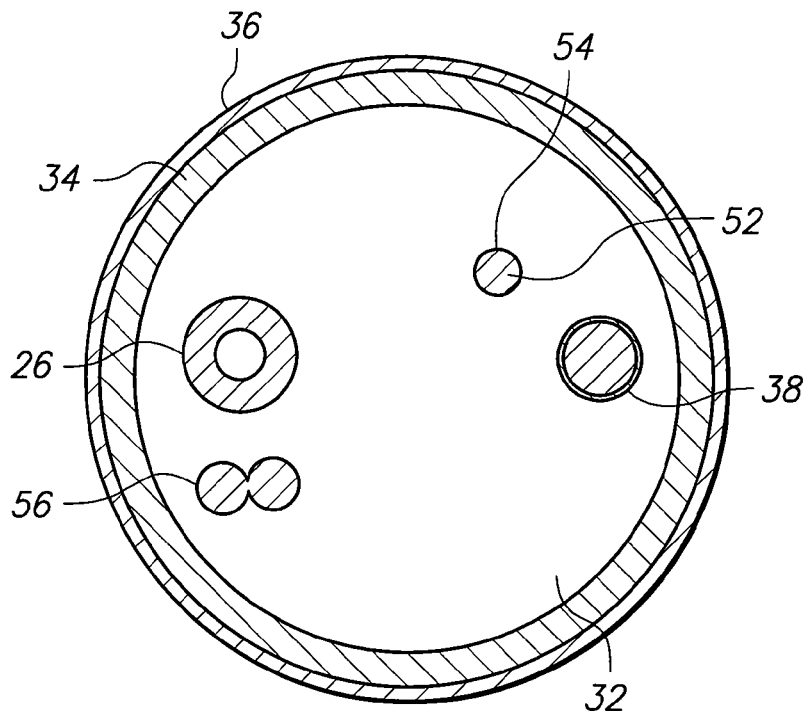
FIG. 3 is a cross-sectional view of the cryo-catheter including internal accessories as seen along line 3-3 in FIG. 2.
Figure 4:
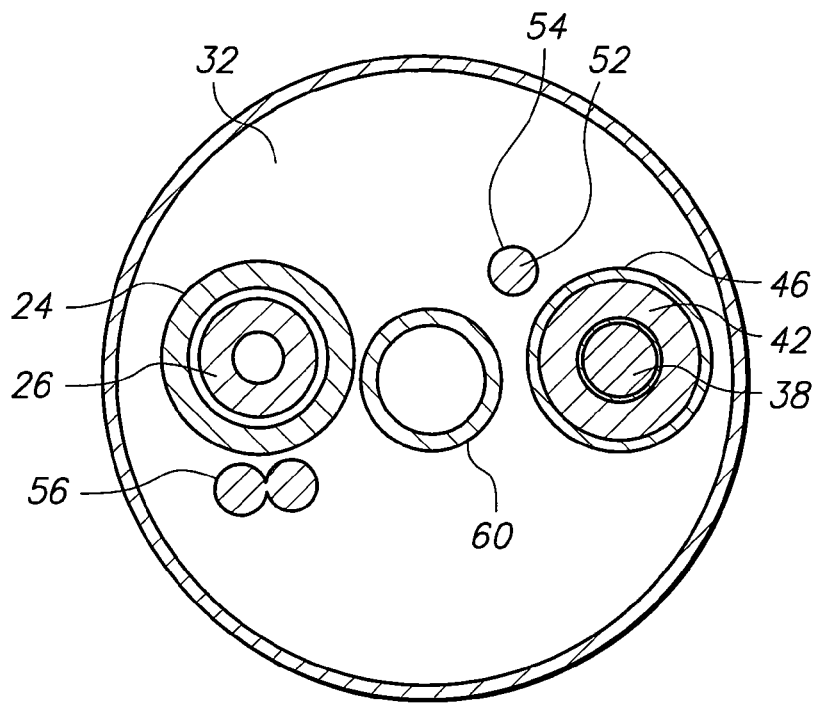
FIG. 4 is a cross-sectional view of the cryo-catheter including internal accessories as seen along line 4-4 in FIG. 2.

Referring now to FIG. 2, a distal portion of the cryo-catheter 12 is shown together with the distal portions of the various internal catheter accessories. A sectional view of the internal catheter accessories that are present in the articulation segment 16 is shown in FIG. 3 and a sectional view of the internal catheter accessories that are present in the braided segment 18 is shown in FIG. 4. As seen in FIG. 2, the cryo-catheter 12 includes the supply line 22 having a high pressure supply tube 24 and a capillary tube 26. In a typical arrangement, the supply tube 24 is sized to impart a negligible impedance to the flow of refrigerant through the supply tube 24. An exemplary supply tube 24 has an inside diameter in the range of 0.017-0.022 inches, an outside diameter in the range of 0.025-0.030 inches and a length of about 73 inches. On the other hand, for the system 10, the capillary tube 26 is typically sized with a much greater impedance than the high pressure supply tube 24, to thereby cause most of the supply line pressure drop to occur in the capillary tube 26. Functionally, this results in a concentration of cooling power at the distal tip 20 of the catheter 12. Comparing FIGS. 3 and 4, it can be seen that the capillary tube 26 has a much smaller inside diameter than the high pressure supply tube 24. As best seen in FIG. 2, the high pressure supply tube 24 terminates at a distal end 28 in the braided section 18. For the embodiment shown, the distal end 28 is located several inches proximal to the articulation segment 16. FIG. 2 also shows that the capillary tube 26 is attached to the distal end 28 of the supply tube 24, extends therefrom through the articulation segment 16, and terminates at a distal end 30 in the distal tip 20. An exemplary capillary tube 26 has an inside diameter in the range of 0.006-0.008 inches, an outside diameter in the range of 0.016-0.018 inches and a length in the range of 4.9 inches to 9.8 inches.

For the system 10 shown in FIG. 1, a refrigerant supply unit (not shown) is attached to the handle 14 to supply a refrigerant to the supply line 22. At the refrigerant supply unit, various valves, pre-cooling circuits, control systems and other components are connected to a refrigerant tank and configured to produce a regulated flow of sub-cooled, liquid refrigerant which is then directed into the supply line 22. In particular, a fluid refrigerant, such as Nitrous Oxide, is used that transitions from a liquid state to a gaseous state as it outflows from the capillary tube 26 to cool the distal tip 20. A suitable refrigerant supply unit for delivering a refrigerant in a liquid state to a supply line 22 for transition to a gaseous state during outflow from a capillary tube 26 is disclosed in co-pending, co-owned U.S. patent application Ser. No. 10/243,997, entitled "A Refrigeration Source for a Cryoablation Catheter" and filed on Sep. 12, 2002. Co-pending U.S. patent application Ser. No. 10/243,997 is hereby incorporated by reference herein. In a typical application, Nitrous Oxide refrigerant is input into the proximal end of the high pressure supply tube 24 at a pressure in the range of about 300 to 500 psi.

With reference to FIG. 2, refrigerant from the supply unit (not shown) traverses the supply tube 24, passes through the capillary tube 26 and then outflows into an expansion chamber formed in the cryo-catheter's distal tip 20. Heat absorbed by the refrigerant during the liquid to gas phase transition (i.e. latent heat) cools the distal tip 20. Expanded refrigerant is then exhausted from the expansion chamber through a low pressure return line. As best seen in FIGS. 3 and 4, the low pressure return line is established in the void spaces 32 that are formed in the central catheter lumen. Typically, suction is applied to the low-pressure return line via an extracorporeally located vacuum pump. Refrigerant suction pressures and flow path dimensions are generally designed to avoid operation of the cryo-catheter 12 in a refrigerant limited condition. Quantitatively, the pressure in the distal portion of the return line is generally maintained in a range between 0.5 atm. and 2 atm.

Comparing FIG. 3 with FIG. 4, it can be seen that the exact nature and dimensions of these void spaces 32 varies along the length of the cryo-catheter 12. Specifically, at each location along the length of the cryo-catheter 12, the available void space 32 will depend on the size and extent of the catheter accessories present in the central lumen at that particular location. These catheter accessories will now be described in greater detail.

With cross reference to FIGS. 2 and 3, an understanding of the articulation segment 16 and the accessories that are present in the articulation segment 16 can be obtained. As shown there, the articulation segment 16 of the cryo-catheter 12 includes a deflection structure 34, which for the embodiment shown is a metal, helically coiled, spring. For the articulation segment 16, the deflection structure 34 is positioned in a flexible outer tube 36. In terms of size, the outer tube 36 has a catheter French size that is in the range of 8-10, allowing the catheter 12 to pass through a patient's vasculature. As detailed further below, the size of the outer tube 36 is preferably as small as possible, subject to the condition that an adequately sized, low pressure return line is established.

With regard to the deflection structure 34, although a spring is shown, it is to be appreciated that other types of deflection structures can be used. For example, a deflection structure made of a thin walled, stainless steel material (e.g. 304 alloy)

that has been cut with a laser to form transverse slits can be used. A more detailed description of the laser cut deflection structure 34 can be found in co-pending, co-owned U.S. patent application Ser. No. 10/774,665, filed Feb. 9, 2004, which is hereby incorporated by reference in its entirety herein and co-pending, co-owned U.S. patent application Ser. No. 10/876,312 which is also hereby incorporated by reference herein.

To deflect the articulation segment 16, the cryo-catheter 12 includes a pull wire 38 having a distal end 40 that is attached to the distal tip 20 and a proximal end (not shown) that is operationally attached to a control wheel (not shown) on the handle 14 (see FIG. 1). In use, the control wheel can be activated to place the pull wire 38 in tension to deflect the distal tip 20. FIGS. 2 and 4 show that a central portion of the pull wire 38 is disposed in a metal, helically coiled, sheath spring 42. The proximal end (not shown) of the sheath spring 42 is rigidly attached to the handle 14 (see FIG. 1), extends therefrom and terminates in a distal end 44 that is located approximately adjacent to the joint where the braided segment 18 attaches to the articulation segment 16. Functionally, the sheath spring 42 provides a compression force in response to the pull wire force, which in turn, allows for articulation of the distal tip 20. An exemplary sheath spring has an inside diameter in the range of 0.008-0.020 inches, an outside diameter in the range of 0.0115-0.025 inches and is made of a wire having a diameter in the range of 0.004-0.006 inches and an overall length of about 40 inches. It can be further seen in FIGS. 2 and 4 that a portion on the sheath spring 42 is disposed within a sheath spring guide tube 46. Typically, the sheath spring guide tube 46 extends from the handle 14 (see FIG. 1) and terminates at a distal end 48 that is located about one and one-half inches proximal to the articulation segment 16. Functionally, the sheath spring guide tube 46 is used for support and to prevent gas leakage into the sheath spring/pull wire assembly.

FIG. 2 also shows that the cryo-catheter 12 includes an EKG band electrode 50 and corresponding electrode wire 52. As shown, for the cryo-catheter 12, the electrode 50 is located near the distal end of the articulation segment 16. From the electrode 50, the electrode wire 52 extends proximally through the central lumen and extends within both the articulation segment 16 and the braided segment 18 (see also FIGS. 3 and 4). From the braided segment 18, the electrode wire 52 typically passes through the handle 14 (see FIG. 1) to an EKG monitor (not shown). For the cryo-catheter 12, the electrode wire 52 is typically a Nickel wire having an outside diameter in the range of 0.008-0.011 inches that is disposed in a polyimide sleeve 54. The use of a sleeve 54 over the wire 52 prevents electrical shorts with other components of the cryo-catheter 12. FIGS. 2 and 3 also show that a thermocouple wire set 56 is disposed in the central lumen of the cryo-catheter 12 to measure a distal tip 20 temperature. As shown, the thermocouple wire set 56 extends through both the braided segment 18 and articulation segment 16 and terminates in a distal end 58 that is located in the distal tip 20. For the cryo-catheter 12, the thermocouple wire set 56 extends through the handle 14 to a temperature monitor (not shown).

As best seen in FIGS. 2 and 4, the cryo-catheter 12 includes a pressure measurement tube 60 that is disposed in the central lumen of the braided segment 18. As shown, the pressure measurement tube 60 has a distal end 62 that is positioned at a location proximal to the joint where the braided segment 18 attaches to the articulation segment 16 (i.e. about 1 inch proximal to the articulation segment 16). From its distal end 62, the pressure measurement tube 60 extends proximally through the handle 14 (see FIG. 1) to a pressure monitor (not shown) which measures a pressure at the proximal end of the pressure measurement tube 60. Together, the pressure measurement tube 60 and pressure monitor cooperate to provide an estimate of the pressure in the low pressure return line near the distal tip 20. An exemplary pressure measurement tube 60 has an inside diameter in the range of 0.017-0.022 inches, an outside diameter in the range of 0.025-0.030 inches and a length of about 73 inches.

As indicated above, an important functional consideration for the cryo-catheter 12 is its ability to transfer a fluid refrigerant to the catheter's distal tip 20 as a liquid, and to then exhaust the refrigerant back through both the articulation segment 16 and the braided segment 18, as a gas. As also indicated above, however, the outside dimensions of the cryo-catheter 12 are constrained by anatomical requirements. Operationally, these outside dimensions necessarily impact on the economies that can be obtained for fluid refrigerant flow inside the cryo-catheter 12. With these constraints in mind, the consequent requirement is that there be the maximum possible void space within the cryo-catheter 12 for exhausting the gas refrigerant from the cryo-catheter 12. Both the articulation segment 16 and the braided segment 18 are involved here.

Table A, shown below, provides exemplary maximum and minimum dimensions for specified components that may be incorporated into the cryo-catheter 12 and positioned in the articulation segment 16. Table A is, perhaps, best appreciated by cross-referencing it with FIG. 3.

TABLE A

|  | Min Meas. | Max Meas. |  |
| --- | --- | --- | --- |
| Deflection Structure (34) | | | |
| Inner Diameter | 7.8E−02 | 7.900E−02 | in. |
| Area | 4.778E−03 | 4.902E−03 | sq. in. |
| Capillary Tube (26) | | | |
| Outer Diameter | 1.600E−02 | 1.800E−02 | in. |
| Area | 2.011E−04 | 2.545E−04 | sq. in. |
| Pull Wire (38) | | | |
| Outer Diameter | 1.0E−02 | 1.100E−02 | in. |
| Area | 7.854E−05 | 9.503E−05 | sq. in. |
| Electrode Wire (52) | | | |
| Outer Diameter | 8.000E−03 | 1.100E−02 | in. |
| Area | 5.027E−05 | 9.503E−05 | sq. in. |
| Thermocouple Wire Set (56) | | | |
| Outer Diameter | 7.000E−03 | 8.000E−03 | in. |
| Area | 3.848E−05 | 5.027E−05 | sq. in. |
| Void Space Area (32) | 4.410E−03 | 4.407E−03 | sq. in. |

Using the numbers provided above, it is easily determined that the void space within the articulation segment 16 will be in a range of about 89.4% to about 91.4% of the space available inside the deflection structure 34 of articulation segment 16.

Similar to Table A, Table B shown below, provides exemplary maximum and minimum dimensions for specified components that may be positioned in the braided segment 18. Table B is, perhaps, best appreciated by cross-referencing it with FIG. 4.

TABLE B

|  | Min Meas. | Max Meas. |  |
|---|---|---|---|
| Catheter Cross Section | | | |
| Inner Diameter | 9.900E−02 | 9.950E−02 | in. |
| Area | 7.698E−03 | 7.776E−03 | sq. in. |
| Supply Tube (24) | | | |
| Outer Diameter | 2.500E−02 | 3.000E−02 | in. |
| Area | 4.909E−04 | 7.069E−04 | sq. in. |
| Spring Sheath (42) | | | |
| Outer Diameter | 1.150E−02 | 2.500E−02 | in. |
| Area | 1.039E−04 | 4.909E−04 | sq. in. |
| Pressure Measuring Tube (60) | | | |
| Outer Diameter | 2.500E−02 | 3.000E−02 | in. |
| Area | 4.909E−04 | 7.069E−04 | sq. in. |
| Electrode Wire (52) | | | |
| Outer Diameter | 8.000E−03 | 1.100E−02 | in. |
| Area | 5.027E−05 | 9.503E−05 | sq. in. |
| Thermocouple Wire Set (56) | | | |
| Outer Diameter | 7.000E−03 | 8.000E−03 | in. |
| Area | 3.848E−05 | 5.027E−05 | sq. in. |
| Void Space Area (32) | 6.524E−03 | 5.726E−03 | sq. in. |

Using the numbers provided above, it is easily determined that the void space within the braided segment 18 will be in a range of about 73.0% to about 84.2% of the space available inside the braided segment 18.

An important observation to be made from Tables A and B is the fact that, although the percentage of void space in articulation segment 16 is greater than the percentage of void space in the braided segment 18, the actual void space in the braided segment 18 is greater. As indicated above, this relationship is established to ensure maximum operational efficiency.

While the particular Cryo-applicator Cross-Section Configuration and corresponding methods of use as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A configuration for a cryo-applicator having a proximal end and a distal end, the configuration comprising:
a catheter shaft including a distal segment having a distal end and a proximal end, a tip at the distal end of said distal segment, and a proximal segment attached to said distal segment, wherein said proximal segment and said distal segment define a central lumen extending through at least a portion of said catheter shaft, wherein said central lumen has a first cross-sectional area in said distal segment and a second cross-sectional area in said proximal segment, wherein the second cross-sectional area of the proximal segment is greater the first cross-sectional area; and
a fluid supply line for transferring a liquid refrigerant through said central lumen of said proximal segment and said distal segment to said tip for boiling the liquid refrigerant in said tip; wherein
a return path for a flow of gaseous refrigerant is defined in said central lumen by a void created between said fluid supply line and said catheter shaft, and further wherein the return path includes a first void space in the proximal segment that is at least about 30% greater in cross-sectional area than a second void space in the distal segment such that a pressure in the return path is substantially equal to a pressure in the tip when the applicator is in use such that the liquid refrigerant is maintained in a liquid state as it flows through the fluid supply line.

2. The configuration as recited in claim 1, wherein said cryo-applicator is a probe for cryoablating exposed tissue.

3. The configuration as recited in claim 1, wherein said cryo-applicator is a cryo-catheter for cryoablating internal tissue.

4. The configuration as recited in claim 1, further comprising an accessory positioned in said central lumen.

5. A configuration for a cryo-catheter having a proximal end and a distal end, the configuration comprising:
a tip at the distal end of said cryo-catheter;
a handle at the proximal end of said cryo-catheter;
an articulation segment attached to said tip;
a braided segment attached to said articulation segment and to said handle, wherein the braided segment and the articulation segment define a central lumen extending between said handle and said tip, and wherein said central lumen has a first cross-sectional area in said articulation segment and a second cross-sectional area in said braided segment, wherein said second cross-sectional area is greater than said first cross-sectional area;
a fluid supply line for transferring a liquid refrigerant through said central lumen of said braided segment and said articulation segment to said tip for boiling the liquid refrigerant in said tip;
a return path for a flow of gaseous refrigerant defined in said central lumen by void space created between said fluid supply line and said catheter shaft, wherein the return path includes a first void space in the braided segment that is at least about 30% greater in cross-sectional area than a second void space in the articulation segment such that a pressure in the return path is substantially equal to a pressure in the tip when the cryo-catheter is in use such that the liquid refrigerant is maintained in a liquid state as it flows through the fluid supply line; and
at least one accessory positioned in said central lumen spaced from each of the fluid supply line and said catheter shaft.

6. The configuration as recited in claim 5, wherein said at least one accessory includes a pull wire.

7. The configuration as recited in claim 5, wherein said at least one accessory includes a thermocouple wire.

8. The configuration as recited in claim 5, wherein said at least one accessory includes an electrode wire.

9. The configuration as recited in claim 5, wherein said at least one accessory includes a deflection system having a pull wire, sheath spring and sheath spring guide tube.

10. The configuration as recited in claim 5, wherein said accessory comprises a pressure measurement tube.

11. The configuration as recited in claim 5, wherein said fluid supply means comprises a hollow supply tube and a capillary tube.

12. The configuration as recited in claim 5, wherein said liquid refrigerant includes nitrous oxide.

13. A cryo-catheter having a proximal end and a distal end, the cryo-catheter comprising:
a tip at the distal end of said cryo-catheter;
a handle at the proximal end of said cryo-catheter;
an articulation segment attached to said tip;

a braided segment attached to said articulation segment and to said handle, said articulation segment and said braided segment defining a central lumen extending between said handle and said tip, and wherein said central lumen has a first cross-sectional area in said articulation segment and a second cross-sectional area in said braided segment, wherein said second cross-sectional area is greater than said first cross-sectional area;

a fluid supply configured to provide a liquid refrigerant through said central lumen to said tip;

a return path for a flow of gaseous refrigerant defined in said central lumen by a void space created between said fluid supply and a wall of the cryo-catheter, wherein the return path includes a first void space in the braided segment that is greater in cross-sectional area than a second void space in the articulation segment such that a pressure in the return path is substantially equal to a pressure in the tip such that the liquid refrigerant is maintained in a liquid state as it flows through the fluid supply; and at least one accessory positioned in said central lumen spaced from each of the fluid supply.

14. The cryo-catheter of claim 13, wherein said at least one accessory includes a pull wire.

15. The cryo-catheter of claim 13, wherein said at least one accessory includes a thermocouple wire.

16. The cryo-catheter of claim 13, wherein said at least one accessory includes an electrode wire.

17. The cryo-catheter of claim 13, wherein said at least one accessory includes a deflection system having a pull wire, sheath spring and sheath spring guide tube.

18. The cryo-catheter of claim 13, wherein said fluid supply comprises a hollow supply tube and a capillary tube.

19. The cryo-catheter of claim 13, wherein said liquid refrigerant includes Nitrous Oxide.

20. The cryo-catheter of claim 13, wherein said at least one accessory comprises a thermocouple wire, an electrode wire and a deflection system having a pull wire, a sheath spring and a sheath spring guide tube.

* * * * *